(12) United States Patent
Asakura

(10) Patent No.: US 11,143,667 B2
(45) Date of Patent: Oct. 12, 2021

(54) AUTOMATIC ANALYZER AND COMPUTER-READABLE RECORDING MEDIUM THAT STORES PROGRAM

(71) Applicant: JEOL Ltd., Tokyo (JP)

(72) Inventor: Makoto Asakura, Tokyo (JP)

(73) Assignee: JEOL Ltd., Tokyo (JP)

( * ) Notice: Subject to any disclaimer, the term of this patent is extended or adjusted under 35 U.S.C. 154(b) by 319 days.

(21) Appl. No.: 15/991,487

(22) Filed: May 29, 2018

(65) Prior Publication Data

US 2018/0348246 A1 Dec. 6, 2018

(30) Foreign Application Priority Data

May 30, 2017 (JP) .............................. JP2017-106557

(51) Int. Cl.
*G01N 35/10* (2006.01)
*G01N 35/04* (2006.01)
(Continued)

(52) U.S. Cl.
CPC ..... *G01N 35/1004* (2013.01); *G01N 35/0092* (2013.01); *G01N 35/02* (2013.01);
(Continued)

(58) Field of Classification Search
CPC ............... G01N 35/1004; G01N 35/02; G01N 35/0092; G01N 35/1002; G01N 35/04;
(Continued)

(56) References Cited

U.S. PATENT DOCUMENTS 4,276,051 A * 6/1981 Ginsberg ......... G01N 35/00732
422/64
6,003,531 A * 12/1999 Kimura .............. G01N 35/1004
134/155
(Continued)

FOREIGN PATENT DOCUMENTS

| JP | 200046844 A | 2/2000 |
| JP | 2015172488 A * | 10/2015 |
| JP | 2016211879 A | 12/2016 |

OTHER PUBLICATIONS

European Search Report dated Oct. 24, 2018 issued in EP 18174932.6.

*Primary Examiner* — Benjamin R Whatley
*Assistant Examiner* — Curtis A Thompson
(74) *Attorney, Agent, or Firm* — The Webb Law Firm

(57) ABSTRACT

An automatic analyzer includes a specimen holding section that holds a specimen container for containing a specimen; a specimen dispensing section that dispenses the specimen from the specimen container into a dilution container; a dilution container holding section that holds the dilution container for containing a diluted specimen, which is the specimen that has been diluted; a diluted specimen dispensing section that dispenses the diluted specimen from the dilution container into a reaction container; and a controlling section that, while the diluted specimen dispensing section dispenses the diluted specimen into the reaction container in (Continued)

accordance with a measurement item, causes the specimen dispensing section to perform a cleaning operation of the specimen dispensing section any number of times by using a cleaning liquid.

6 Claims, 7 Drawing Sheets

(51) Int. Cl.
*G01N 35/02* (2006.01)
*G01N 35/00* (2006.01)
G01N 33/493 (2006.01)
B01L 3/00 (2006.01)
G01N 1/14 (2006.01)

(52) U.S. Cl.
CPC ......... *G01N 35/04* (2013.01); *G01N 35/1002* (2013.01); *B01L 3/00* (2013.01); *G01N 1/14* (2013.01); *G01N 33/493* (2013.01); *G01N 35/00* (2013.01); *G01N 35/10* (2013.01); *G01N 2035/0432* (2013.01); *G01N 2035/1032* (2013.01)

(58) Field of Classification Search
CPC ........ G01N 35/00; G01N 33/493; G01N 1/14; G01N 35/10; G01N 2035/0432; G01N 2035/1032; B01L 3/00
See application file for complete search history.

(56) References Cited

U.S. PATENT DOCUMENTS

| | | | |
|---|---|---|---|
| 6,317,718 B1* | 11/2001 | Fano | G06Q 10/109 |
| | | | 705/14.39 |
| 2002/0106814 A1* | 8/2002 | Matsubara | G01N 35/026 |
| | | | 436/180 |
| 2005/0074363 A1* | 4/2005 | Dunfee | G01N 35/1004 |
| | | | 422/81 |
| 2009/0133512 A1* | 5/2009 | Kuroda | G01N 35/1016 |
| | | | 73/863.01 |
| 2012/0318302 A1* | 12/2012 | Nakayama | G01N 35/1004 |
| | | | 134/26 |
| 2015/0204895 A1* | 7/2015 | Yasui | G01N 35/1004 |
| | | | 422/64 |
| 2015/0309060 A1* | 10/2015 | Tamagawa | G01N 35/0092 |
| | | | 436/166 |
| 2015/0355209 A1* | 12/2015 | Tomii | G01N 35/00584 |
| | | | 436/43 |
| 2016/0187365 A1* | 6/2016 | Yaita | G01N 35/1004 |
| | | | 436/43 |
| 2016/0290991 A1* | 10/2016 | Okamura | G01N 15/1459 |
| 2019/0041415 A1* | 2/2019 | Nonaka | G01N 35/1004 |

* cited by examiner

FIG. 4

SPECIMEN CONTAMINATION PREVENTION SETTING

| PROBE CLEANING | CLEANING AGENT NUMBER | NUMBER OF CLEANING OPERATIONS |
|---|---|---|
| ✓ | 1  2 | 1 |
|   | 2  4 | 1 |

| DEVICE OPERATION CYCLE | DILUTION CONTAINER ORIGINAL SPECIMEN DISPENSING OPERATION | ORIGINAL SPECIMEN SAMPLING PROBE | STIRRING OPERATION | DILUTION CONTAINER DILUTED SPECIMEN DISPENSING OPERATION | DILUTED SPECIMEN SAMPLING PROBE |
|---|---|---|---|---|---|
| (1) ↓ | ADVANCE ONE STEP | SPECIMEN A DISPENSING OPERATION | SPECIMEN Z STIRRING OPERATION | ADVANCE ONE STEP | SPECIMEN Y DISPENSING OPERATION |
| (2) ↓ | — | SUCK IN CLEANING AGENT AND DISCHARGE CLEANING AGENT TO CLEANING MECHANISM | SPECIMEN A STIRRING OPERATION | ADVANCE ONE STEP | SPECIMEN Z DISPENSING OPERATION |
| (3) ↓ | ADVANCE ONE STEP | SPECIMEN B DISPENSING OPERATION | — | ADVANCE ONE STEP | SPECIMEN A DISPENSING OPERATION (ITEM 1) |
| (4) ↓ | — | SUCK IN CLEANING AGENT AND DISCHARGE CLEANING AGENT TO CLEANING MECHANISM | SPECIMEN B STIRRING OPERATION | — | SPECIMEN A DISPENSING OPERATION (ITEM 2) |
| (5) ↓ | ADVANCE ONE STEP | SPECIMEN C DISPENSING OPERATION | — | — | SPECIMEN A DISPENSING OPERATION (ITEM 3) |
| (6) ↓ | — | SUCK IN CLEANING AGENT AND DISCHARGE CLEANING AGENT TO CLEANING MECHANISM | SPECIMEN C STIRRING OPERATION | ADVANCE ONE STEP | SPECIMEN B DISPENSING OPERATION (ITEM 1) |
| (7) ↓ | ADVANCE ONE STEP | SPECIMEN D DISPENSING OPERATION | — | — | SPECIMEN B DISPENSING OPERATION (ITEM 2) |

FIG. 6A

| DEVICE OPERATION CYCLE | DILUTION CONTAINER ORIGINAL SPECIMEN DISPENSING OPERATION | ORIGINAL SPECIMEN SAMPLING PROBE | STIRRING OPERATION | DILUTION CONTAINER DILUTED SPECIMEN DISPENSING OPERATION | DILUTED SPECIMEN SAMPLING PROBE |
|---|---|---|---|---|---|
| (1) ↓ | ADVANCE ONE STEP | SPECIMEN A DISPENSING OPERATION | SPECIMEN Z STIRRING OPERATION | ADVANCE ONE STEP | SPECIMEN Y DISPENSING OPERATION |
| (2) ↓ | — | SUCK IN CLEANING AGENT AND DISCHARGE CLEANING AGENT TO CLEANING MECHANISM (FIRST TIME) | SPECIMEN A STIRRING OPERATION | ADVANCE ONE STEP | SPECIMEN Z DISPENSING OPERATION |
| (3) ↓ | — | SUCK IN CLEANING AGENT AND DISCHARGE CLEANING AGENT TO CLEANING MECHANISM (SECOND TIME) | — | ADVANCE ONE STEP | SPECIMEN A DISPENSING OPERATION (ITEM 1) |
| (4) ↓ | — | SUCK IN CLEANING AGENT AND DISCHARGE CLEANING AGENT TO CLEANING MECHANISM (THIRD TIME) | — | — | SPECIMEN A DISPENSING OPERATION (ITEM 2) |
| (5) ↓ | — | SUCK IN CLEANING AGENT AND DISCHARGE CLEANING AGENT TO CLEANING MECHANISM (FOURTH TIME) | — | — | SPECIMEN A DISPENSING OPERATION (ITEM 3) |
| (6) ↓ | ADVANCE ONE STEP | SPECIMEN B DISPENSING OPERATION | — | — | — |
| (7) ↓ | — | SUCK IN CLEANING AGENT AND DISCHARGE CLEANING AGENT TO CLEANING MECHANISM (FIRST TIME) | SPECIMEN B STIRRING OPERATION | — | — |
| (8) ↓ | ADVANCE ONE STEP | SPECIMEN C DISPENSING OPERATION | — | ADVANCE ONE STEP | SPECIMEN B DISPENSING OPERATION (ITEM 1) |

FIG. 6B

| DEVICE OPERATION CYCLE | DILUTION CONTAINER ORIGINAL SPECIMEN DISPENSING OPERATION | ORIGINAL SPECIMEN SAMPLING PROBE | STIRRING OPERATION | DILUTION CONTAINER DILUTED SPECIMEN DISPENSING OPERATION | DILUTED SPECIMEN SAMPLING PROBE |
|---|---|---|---|---|---|
| (1) ↓ | ADVANCE ONE STEP | SPECIMEN A DISPENSING OPERATION | SPECIMEN Z STIRRING OPERATION | ADVANCE ONE STEP | SPECIMEN Y DISPENSING OPERATION |
| (2) ↓ | — | SUCK IN CLEANING AGENT AND DISCHARGE CLEANING AGENT TO CLEANING MECHANISM (FIRST TIME) | SPECIMEN A STIRRING OPERATION | ADVANCE ONE STEP | SPECIMEN Z DISPENSING OPERATION |
| (3) ↓ | — | SUCK IN CLEANING AGENT AND DISCHARGE CLEANING AGENT TO CLEANING MECHANISM (SECOND TIME) | — | ADVANCE ONE STEP | SPECIMEN A DISPENSING OPERATION (ITEM 1) |
| (4) ↓ | ADVANCE ONE STEP | SPECIMEN B DISPENSING OPERATION | — | — | SPECIMEN A DISPENSING OPERATION (ITEM 2) |
| (5) ↓ | — | SUCK IN CLEANING AGENT AND DISCHARGE CLEANING AGENT TO CLEANING MECHANISM (FIRST TIME) | SPECIMEN B STIRRING OPERATION | — | SPECIMEN A DISPENSING OPERATION (ITEM 3) |
| (6) ↓ | ADVANCE ONE STEP | SPECIMEN C DISPENSING OPERATION | — | ADVANCE ONE STEP | SPECIMEN B DISPENSING OPERATION (ITEM 1) |

AUTOMATIC ANALYZER AND COMPUTER-READABLE RECORDING MEDIUM THAT STORES PROGRAM

CROSS-REFERENCE TO RELATED APPLICATION

This application claims priority to Japanese Patent Application No. 2017-106557 filed May 30, 2017, the disclosure of which is hereby incorporated in its entirety by reference.

BACKGROUND OF THE INVENTION

Field of the Invention

The present invention relates to an automatic analyzer that analyzes, for example, various components in the blood, urine, etc., of a patient, and to a computer-readable recording medium that stores a program.

Description of Related Art

When an original specimen (also referred to as "specimen") to which an automatic analyzer gives an extremely high measurement value is measured, the usual cleaning alone performed on an original specimen sampling probe that dispenses an original specimen is not enough to remove the influence of an original specimen previously dispensed by the original specimen sampling probe on the measurement value of an original specimen dispensed by the original specimen sampling probe this time and to remove contamination of the original specimen. A phenomenon in which the influence of a specimen having a high measurement value and previously adhered to the original specimen sampling probe remains in the original specimen sampling probe and appears as a high measurement value when measuring the next specimen is called "carry-over".

When a carry-over between original specimens (an inter-specimen carry-over) occurs, various effects occur. For example, effects resulting from an inter-specimen carry-over are listed in (A) and (B) below: (A) Due to a carry-over via the original specimen sampling probe, an original specimen is contaminated. (B) Due to a carry-over via the original specimen sampling probe, the measurement value of a dispensed original specimen is affected.

When, in measuring a plurality of specimens, the occurrence of an inter-specimen carry-over is suspected and it is judged that the inter-specimen carry-over has an influence on a measurement value, the specimens are retested, and the adequacy of the results of measurement is checked. When it is obvious that the occurrence of the inter-specimen carry-over has an influence on the results of measurement, the original specimen sampling probe is cleaned by using, for example, a special cleaning agent.

An automatic analyzer that prevents contamination of an original specimen by using a disposable probe as the original specimen sampling probe exists. In addition, there exists a method of preventing contamination of an original specimen by cleaning the original specimen sampling probe as a result of preparing a dummy item where a cleaning agent is set for, for example, a diluting liquid and sucking the cleaning agent that has been set in the dummy item between specimens that are to be measured. Further, when it is obvious that the occurrence of an inter-specimen carry-over has an influence on the results of measurement, a WASH function of a device (that is, a function of cleaning all containers, probes, and stirring rods) is sometimes executed.

Japanese Unexamined Patent Application Publication No. 2000-46844 discloses an automatic analyzer that performs a special cleaning operation and that realizes increased cleaning efficiency as a result of increasing cleaning time by adding a special cleaning equivalent time to a usual nozzle cleaning operation.

In recent years, in an automatic analyzer that is used in biochemical analysis, a carry-over rate on the order that does not influence measurement values is being realized. However, with the diversification of measurement items, there is a demand for, for example, increasing highly sensitive items, allowing operations requiring mixed measurements of different specimen materials, and dealing with cases when an original specimen measured by a biochemical analyzer is to be measured by another analyzer. Therefore, it is necessary for the carry-over rate to be on the order that is smaller than carry-over rates up until now.

In order to reduce the carry-over rate, it is necessary to increase the cleaning capability with respect to the original specimen sampling probe and a dilution container for containing an original specimen. However, while there is a demand for an increase in the processing capability (the number of tests per hour) of the automatic analyzer and while it is necessary to increase the speed of an analyzing operation, it is difficult to perform a high-level cleaning operation. In addition, it is necessary to previously set the cleaning operation (such as the use of a cleaning agent) and the number of cleaning operations to allow the automatic analyzer to perform a high-level cleaning operation.

By dispensing an original specimen by using the aforementioned disposable probe, it is possible to prevent contamination of the original specimen. However, it is necessary to replace the used disposable probe with a new disposable probe each time an original specimen is to be dispensed. Therefore, it takes time for the processing operation of the entire automatic analyzer to be completed, as a result of which it is difficult to realize a dispensation precision and a high processing capability that are demanded by a user. In addition, when a special cleaning function, such as the aforementioned WASH function, is used, the cleaning time is longer than the usual cleaning time, as a result of which the processing capability of the automatic analyzer is reduced.

A method of determining that the measurement value of a certain specimen is influenced by a previously measured specimen, and of re-measuring (re-testing) the certain specimen not only requires a long time until the automatic analyzer informs a user of the measurement value, but also increases the amount of reagent that is consumed due to the re-measurement. In addition, due to the difference in the specimen materials to be measured, the influence of an inter-specimen carry-over is a concern depending upon the measurement item.

Although the automatic analyzer has prevented an inter-specimen carry-over by performing an operation including measures, such as measuring a dummy item, when the measurement of a measurement item is delayed due to the measurement of a dummy item, the processing capability of the automatic analyzer is reduced.

In addition, the automatic analyzer disclosed in Japanese Unexamined Patent Application Publication No. 2000-46844 does not include a specimen diluting mechanism. Therefore, when the special cleaning that takes longer than the usual cleaning is performed, an operation in which a sample nozzle discharges a specimen to a reaction section is stopped. Consequently, the processing capability of the automatic analyzer is reduced.

SUMMARY OF THE INVENTION

In view of such circumstances, it is an object of the present invention to, for example, make it possible to prevent contamination of an original specimen caused by an inter-specimen carry-over, and reduce a reduction in the processing capability of an automatic analyzer.

An automatic analyzer according to the present invention includes a specimen holding section that holds a specimen container for containing a specimen; a specimen dispensing section that dispenses the specimen from the specimen container into a dilution container; a dilution container holding section that holds the dilution container for containing a diluted specimen, which is the specimen that has been diluted; a diluted specimen dispensing section that dispenses the diluted specimen from the dilution container into a reaction container; and a controlling section that, while the diluted specimen dispensing section dispenses the diluted specimen into the reaction container in accordance with a measurement item, causes the specimen dispensing section to perform a cleaning operation of the specimen dispensing section any number of times by using a cleaning liquid.

According to the present invention, it is possible to execute a measurement operation of the diluted specimen dispensing section without influencing the cleaning operation of the specimen dispensing section, and to efficiently clean the specimen dispensing section without reducing the processing capability of the automatic analyzer, for example, to prevent contamination of an original specimen caused by an inter-specimen carry-over.

The above-described automatic analyzer is one form of the present invention, and a computer-readable recording medium that stores a program reflecting an aspect of the present invention also has a structure that is similar to that of the automatic analyzer reflecting an aspect of the present invention.

Problems, structures, and effects other than those mentioned above are made clear by the description of the embodiments below.

BRIEF DESCRIPTION OF THE DRAWINGS

FIG. 4 is a structural view of a specimen contamination prevention setting screen according to the first embodiment of the present invention.

FIG. 5 is an explanatory view showing that, after the biochemical analyzer according to the first embodiment of the present invention has measured a specimen A, an original specimen contamination prevention operation is required when measuring a specimen B.

FIGS. 6A and 6B are each an explanatory view showing that, after a biochemical analyzer according to a second embodiment of the present invention has dispensed a specimen A, a dilution container is cleaned a plurality of times before dispensing a specimen B.

DESCRIPTION OF THE INVENTION

Figure 1:
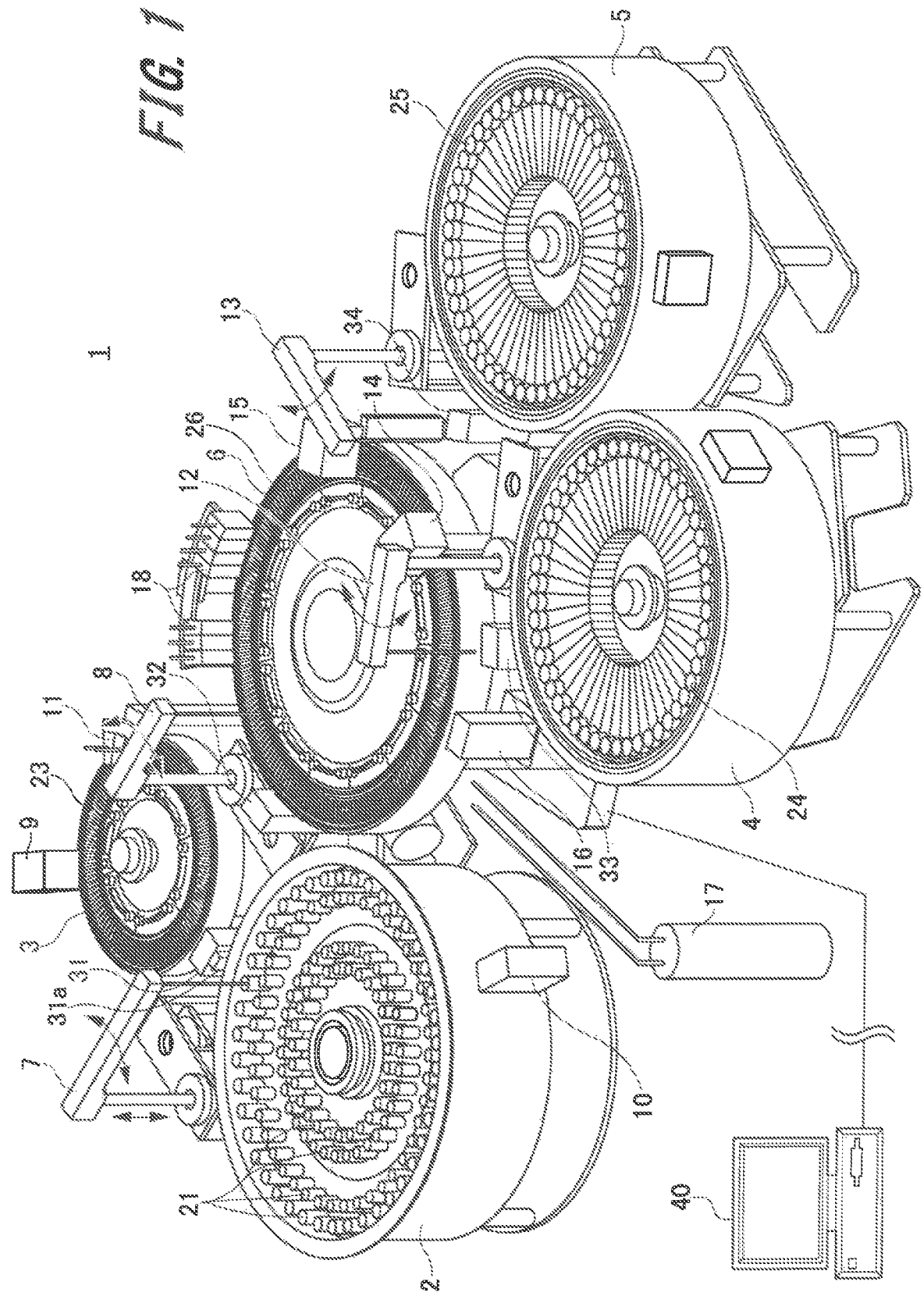
FIG. 1 is an explanatory view that schematically shows an automatic analyzer according to a first embodiment of the present invention.

Modes for carrying out the present invention are described below with reference to the attached drawings. In the specification and the drawings, structural elements having substantially the same function or structure are given the same reference numerals, and the same descriptions thereof are not repeated.

1. First Embodiment 1-1. Structure of Automatic Analyzer

First, an automatic analyzer according to an embodiment is described with reference to FIG. 1.

FIG. 1 is an explanatory view that schematically shows the automatic analyzer according to the embodiment.

The device shown in FIG. 1 is a biochemical analyzer 1 that is applied as an example of the automatic analyzer of the present invention. The biochemical analyzer 1 is a device that automatically measures the amount of a particular component that is contained in a specimen that is extracted from living matter, such as blood or urine.

In the biochemical analyzer 1 including a dilution mechanism that is capable of diluting a specimen by a diluting liquid, there is concern about an original specimen becoming contaminated on the basis of an inter-specimen carry-over, where an original specimen sampling probe 7 causes an original specimen that is contained in a sample container 21 to be contaminated by an original specimen that is contained in another sample container 21. Therefore, the biochemical analyzer 1 according to the embodiment outputs a highly reliable measurement value by performing an original specimen contamination prevention operation based on the inter-specimen carry-over.

The biochemical analyzer 1 includes a sample turntable 2, a dilution turntable 3, a first turntable 4, a second turntable 5, and a reaction turntable 6. The biochemical analyzer 1 also includes an original specimen sampling probe 7, a diluted specimen sampling probe 8, a dilution stirring mechanism 9, a sample barcode reader 10, a dilution container cleaning mechanism 11, a first reagent dispensing probe 12, a second reagent dispensing probe 13, a first reaction liquid stirring mechanism 14, a second reaction liquid stirring mechanism 15, a multi-wavelength photometer 16, a constant temperature bath 17, a reaction container cleaning mechanism 18, and a controlling device 40. The biochemical analyzer 1 further includes an original specimen sampling probe cleaning mechanism 31, a diluted specimen sampling probe cleaning mechanism 32, a first reagent probe cleaning mechanism 33, and a second reagent dispensing probe cleaning mechanism 34. In the biochemical analyzer 1, one unit of repetition of, for example, an operation of dispensing a specimen by various probes, such as the diluted specimen sampling probe 8, and a stirring operation by the first reaction liquid stirring mechanism 14 or the second reaction liquid stirring mechanism 15 is performed for a time of one cycle.

The sample turntable 2, the dilution turntable 3, the first turntable 4, the second turntable 5, and the reaction turntable 6 are rotatably supported along a peripheral direction by a driving mechanism (not shown), and rotate at a predetermined speed in each predetermined angular range in the peripheral direction.

The sample turntable 2 (an example of a specimen holding section) holds sample containers 21 that contain specimens (examples of specimen containers). The sample turntable 2 accommodates the sample containers 21 arranged along a circumference of the sample turntable 2. The sample containers 21 contain a specimen, a cleaning agent, and a physiological saline solution, which is a usual diluting liquid. In the description below, although a cleaning agent is used as an example of a cleaning liquid, as the cleaning liquid, internal water that flows into the original specimen sampling probe 7 is also included.

The dilution turntable 3 (an example of a dilution container holding section) accommodates a plurality of dilution containers 23 that are arranged in a peripheral direction of the dilution turntable 3. The dilution containers 23 contain a specimen that has been diluted (diluted specimen) sucked in from the sample containers 21 disposed in the sample turntable 2.

The first turntable 4 (an example of a first reagent container holding section) accommodates a plurality of first reagent containers 24 that are arranged in a peripheral direction of the first turntable 4. The second turntable 5 (an example of a second reagent container holding section) accommodates a plurality of second reagent containers 25 that are arranged in a peripheral direction of the second turntable 5. The first reagent containers 24 contain a first reagent. The second reagent containers 25 contain a second reagent. The first reagent contained in each first reagent container 24 and the second reagent contained in each second reagent container 25 are kept cool at a predetermined temperature by a cooling mechanism (not shown).

The reaction turntable 6 (an example of a reaction container holding section) is disposed between the dilution turntable 3, the first turntable 4, and the second turntable 5. The reaction turntable 6 accommodates a plurality of reaction containers 26 that are arranged in a peripheral direction of the reaction turntable 6. The reaction turntable 6 intermittently moves the reaction containers 26 that it holds. The diluted specimen that has been sampled from a dilution container 23 in the dilution turntable 3, the first reagent that has been sampled from a first reagent container 24 in the first turntable 4, and the second reagent that has been sampled from a second reagent container 25 in the second turntable 5 are injected into a reaction container 26. Then, in the reaction container 26, the diluted specimen and the first reagent and the second reagent are stirred and react with each other.

The original specimen sampling probe 7 (an example of a specimen dispensing section) is disposed in the vicinity of the sample turntable 2 and the dilution turntable 3, and is supported by a dilution probe driving mechanism (not shown) so as to be movable in an axial direction (for example, an up-down direction) of the sample turntable 2 and the dilution turntable 3. The original specimen sampling probe 7 sucks in a predetermined amount of a specimen or a liquid such as a cleaning agent from a sample container 21, and discharges the sucked specimen and a diluting agent (such as a physiological saline solution) of a predetermined amount that is supplied from the original specimen sampling probe 7 itself to a dilution container 23. This causes the specimen to be diluted to a concentration of a predetermined multiple in the dilution container 23. In this way, the original specimen sampling probe 7 dispenses the specimen to the dilution container 23 primarily for the purpose of diluting the specimen.

The original specimen sampling probe 7 can be cleaned by sucking in a cleaning agent from a sample container 21 or a cleaning agent coming-out port 31a, and by using the cleaning agent. Since the original specimen sampling probe 7 is capable of sucking in a cleaning agent from a sample container 21 that contains the cleaning agent, the sample containers 21 that contain a cleaning agent are used as examples of cleaning liquid supplying sections. The cleaning agent coming-out port 31a is a mechanism that is provided near the original specimen sampling probe cleaning mechanism 31, and is where the cleaning agent comes out. Therefore, the original specimen sampling probe 7 is capable of sucking in the cleaning agent from the cleaning agent coming-out port 31a. Consequently, even the cleaning agent coming-out port 31a is used as an example of a cleaning liquid supplying section. When cleaning liquid containers that contain cleaning agents are provided near the original specimen sampling probe cleaning mechanism 31, the original specimen sampling probe 7 is capable of sucking in the cleaning agents from the cleaning liquid containers. Such cleaning liquid containers are also used as examples of cleaning liquid supplying sections. By control of a controlling section 41 shown in FIG. 3 and described later, while the diluted specimen sampling probe 8 dispenses a diluted specimen into a reaction container 26 in accordance with a measurement item, a cleaning operation of the original specimen sampling probe 7 is performed any number of times by using a cleaning agent that the original specimen sampling probe 7 has sucked in from a sample container 21 or the cleaning agent coming-out port 31a.

The original specimen sampling probe 7 is cleaned by the original specimen sampling probe cleaning mechanism 31 (an example of a first cleaning section) that is provided between the sample turntable 2 and the dilution turntable 3. As long as the cleaning of the original specimen sampling probe 7 is set, the controlling section 41 allows the cleaning agent sucked in by the original specimen sampling probe 7 from a sample container 21 or the cleaning agent coming-out port 31a to be discharged to the original specimen sampling probe cleaning mechanism 31 and discarded. By this, the cleaning agent is not discharged to the dilution containers 23, so that the dilution containers 23 can be used for measuring specimens to improve the efficiency with which the dilution turntable 3 is used.

The diluted specimen sampling probe 8 (an example of a diluted specimen dispensing section) is disposed between the dilution turntable 3 and the reaction turntable 6. The diluted specimen sampling probe 8 is supported by a sampling probe driving mechanism (not shown) so as to be movable and rotatable in an axial direction (up-down direction) and a horizontal direction of the dilution turntable 3. The diluted specimen sampling probe 8 sucks in a predetermined amount of diluted specimen from a dilution container 23 in the dilution turntable 3, and discharges the sucked-in diluted specimen into a reaction container 26 in the reaction turntable 6. The diluted specimen sampling probe 8 is cleaned by the diluted specimen sampling probe cleaning mechanism 32 (an example of a second cleaning section) that is provided between the dilution turntable 3 and the reaction turntable 6. However, as long as a dilution container 23 contains a cleaning agent, when the diluted specimen sampling probe 8 sucks in the cleaning agent from the dilution container 23, it is possible to clean the diluted specimen sampling probe 8.

The dilution stirring mechanism 9 and the dilution container cleaning mechanism 11 are disposed in the vicinity of the dilution turntable 3. At the dilution stirring mechanism 9, a stirring rod (not shown) is inserted into a dilution container 23, and a specimen and a diluting liquid are stirred.

In addition, if the dilution container 23 contains a cleaning agent, regarding the dilution stirring mechanism 9, when the stirring rod (not shown) is inserted into the dilution container 23, it is possible to clean the stirring rod. The dilution container cleaning mechanism 11 supplies the cleaning agent to a dilution container cleaning nozzle from a cleaning agent pump, and discharges the cleaning agent into the dilution container 23 from the dilution container cleaning nozzle.

In addition, when, by control of the controlling section 41, the cleaning agent that has been sucked in by the original specimen sampling probe 7 from a sample container 21 or the cleaning agent coming-out port 31a is discharged to a dilution container 23, it is possible to clean a stirrer of the dilution stirring mechanism 9 and the diluted specimen sampling probe 8 by using the cleaning agent that is contained in the dilution container 23. However, when the dilution container 23 contains the cleaning agent, an original specimen can no longer be dispensed into this cell. Therefore, in accordance with the purpose regarding a carry-over that is to be prevented, whether the original specimen sampling probe 7 is to discharge a cleaning agent to the original specimen sampling probe cleaning mechanism 31 or to a dilution container 23 can be set by a user.

The sample barcode reader 10 is provided on a side surface of the sample turntable 2. The sample barcode reader 10 reads a barcode on a side surface of a sample container 21 that is accommodated in the sample turntable 2, and controls, for example, a specimen or a diluting liquid contained in the sample container 21.

The first reagent dispensing probe 12 (an example of a first reagent dispensing section) is disposed between the reaction turntable 6 and the first turntable 4. The first reagent dispensing probe 12 is supported by a first reagent probe driving mechanism (not shown) so as to be movable and rotatable in an axial direction (up-down direction) and a horizontal direction of the reaction turntable 6. The first reagent dispensing probe 12 sucks in a predetermined amount of a liquid, such as a first reagent, from a first reagent container 24 that is at a previously set suction position, and discharges the sucked-in first reagent to a reaction container 26 that is at a previously set position. The first reagent dispensing probe 12 is cleaned by the first reagent probe cleaning mechanism 33 (an example of a third cleaning section) that is provided between the reaction turntable 6 and the first turntable 4.

The first reagent dispensing probe 12 is capable of sucking in a cleaning agent that is contained in a first reagent container 24 and discharging the cleaning agent to a reaction container 26.

The second reagent dispensing probe 13 (an example of a second reagent dispensing section) is disposed between the reaction turntable 6 and the second turntable 5. The second reagent dispensing probe 13 is supported by a second reagent dispensing probe driving mechanism (not shown) so as to be movable and rotatable in an axial direction (up-down direction) and a horizontal direction of the reaction turntable 6. The second reagent dispensing probe 13 sucks in a predetermined amount of a second reagent from a second reagent container 25 in the second turntable 5, and discharges the sucked-in second reagent into a reaction container 26 in the reaction turntable 6. The second reagent dispensing probe 13 is cleaned by the second reagent dispensing probe cleaning mechanism 34 (an example of a fourth cleaning section) that is provided between the reaction turntable 6 and the second turntable 5.

The second reagent dispensing probe 13 is capable of sucking in a cleaning agent that is contained in a second reagent container 25 and discharging the cleaning agent to a reaction container 26.

The first reaction liquid stirring mechanism 14, the second reaction liquid stirring mechanism 15, and the reaction container cleaning mechanism 18 are disposed in the vicinity of the reaction turntable 6. At the first reaction liquid stirring mechanism 14 (an example of a first stirring section), a stirring rod (not shown) is inserted into a reaction container 26 to stir a specimen and a first reagent. At the second reaction liquid stirring mechanism 15 (an example of a second stirring section), a stirring rod (not shown) is inserted into the reaction container 26 to stir a liquid mixture of the specimen, the first reagent, and a second reagent. The reaction container cleaning mechanism 18 cleans the inside of the reaction container 26 where the testing has been completed.

The multi-wavelength photometer 16 is disposed in the vicinity of the reaction turntable 6 so as to oppose an outer wall of the reaction turntable 6, and is used as a light source lamp that applies a light beam to a reaction container. The multi-wavelength photometer 16 performs optical measurement (colorimetric measurement) on a specimen that has been injected into a reaction container 26 and that has reacted with a first reagent and a second reagent, outputs numerical data in which the amounts of various components in the specimen are called "absorbance", and detects the reaction state of the specimen. The controlling device 40 for controlling the operation of each portion of the biochemical device 1 is connected to the multi-wavelength photometer 16.

The constant temperature bath 17 is disposed in the vicinity of the reaction turntable 6. The constant temperature bath 17 keeps the temperature of each reaction container 26 that is provided in the reaction turntable 6 at a certain temperature at all times.

Figure 2:
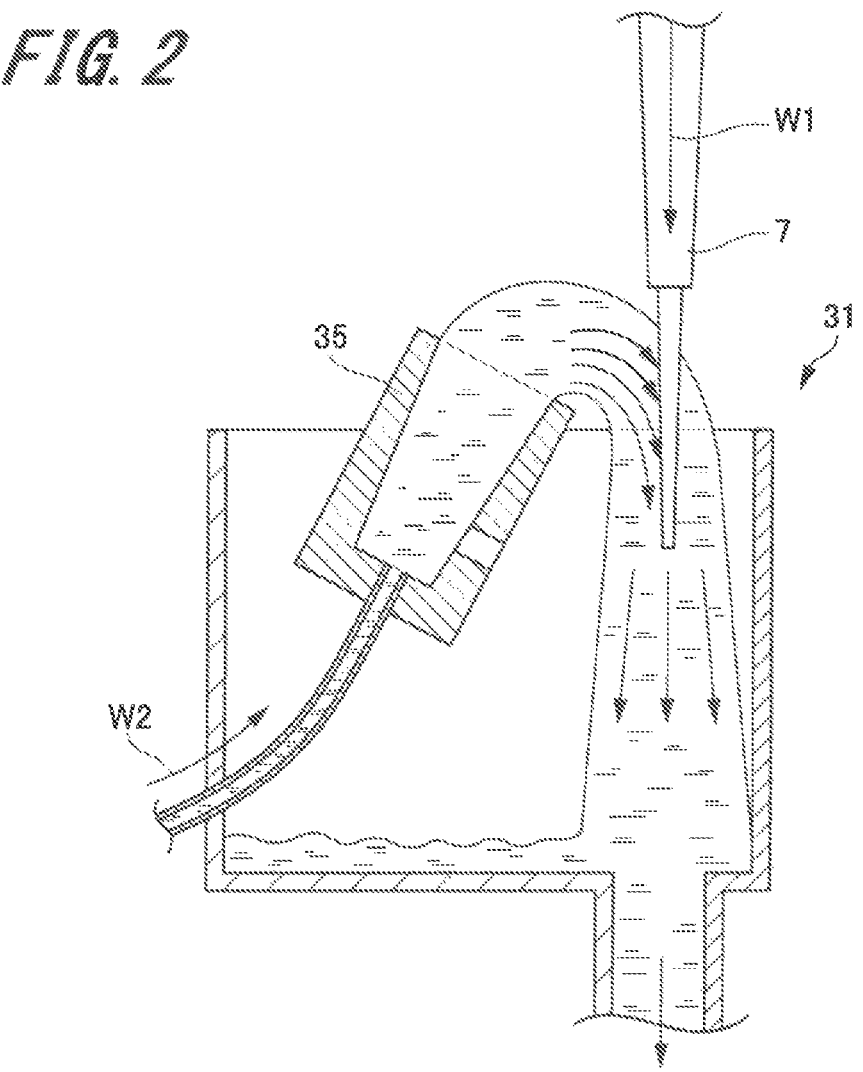
FIG. 2 is a sectional view of an example of an operation of an original specimen sampling probe cleaning mechanism according to the first embodiment of the present invention.

1-2. Example of Operation of Original Specimen Sampling Probe Cleaning Mechanism FIG. 2 is a sectional view of an example of an operation of the original specimen sampling probe cleaning mechanism 31.

After the original specimen sampling probe 7 has dispensed an original specimen into a dilution container 23, in order to prevent a carry-over based on the original specimen, the cleaning operation of the original specimen sampling probe 7 is performed by the original specimen sampling probe cleaning mechanism 31. In order to clean the original specimen sampling probe 7, it is possible to realize a setting in which different cleaning methods are continuously performed.

For example, an end of the original specimen sampling probe 7 that has sucked out a cleaning agent from a sample container 21 in the sample turntable 2 or the cleaning agent coming-out port 31a is moved to a cleaning port of the original specimen sampling probe cleaning mechanism 31. Then, external water W2 (pure water) that has been discharged from a pure water nozzle 35 of the original specimen sampling probe cleaning mechanism 31 cleans the end of the original specimen sampling probe 7.

In addition, internal water W1 that contains the cleaning agent is discharged from the inside of the original specimen sampling probe 7. The internal water W1 and the external water W2 that have cleaned the original specimen sampling probe 7 are discharged from a water-discharge port that is provided at a lower portion of a cleaning port. At this time, the cleaning agent that has been sucked in by the original specimen sampling probe 7 is also discharged along with the internal water W1 to the water-discharge port. In this way, the original specimen on an inner surface and an outer surface of the original specimen sampling probe 7 is cleaned away, and the original specimen sampling probe 7 is used again.

The diluted specimen sampling probe cleaning mechanism 32, the first reagent probe cleaning mechanism 33, and the second reagent dispensing probe cleaning mechanism 34 have structures that are the same as the structure of the original specimen sampling probe cleaning mechanism 31, and are capable of cleaning their corresponding probes.

1-3. Example of Structure of Controlling Device

Next, an example of a structure of the controlling device 40 is described.

Figure 3:
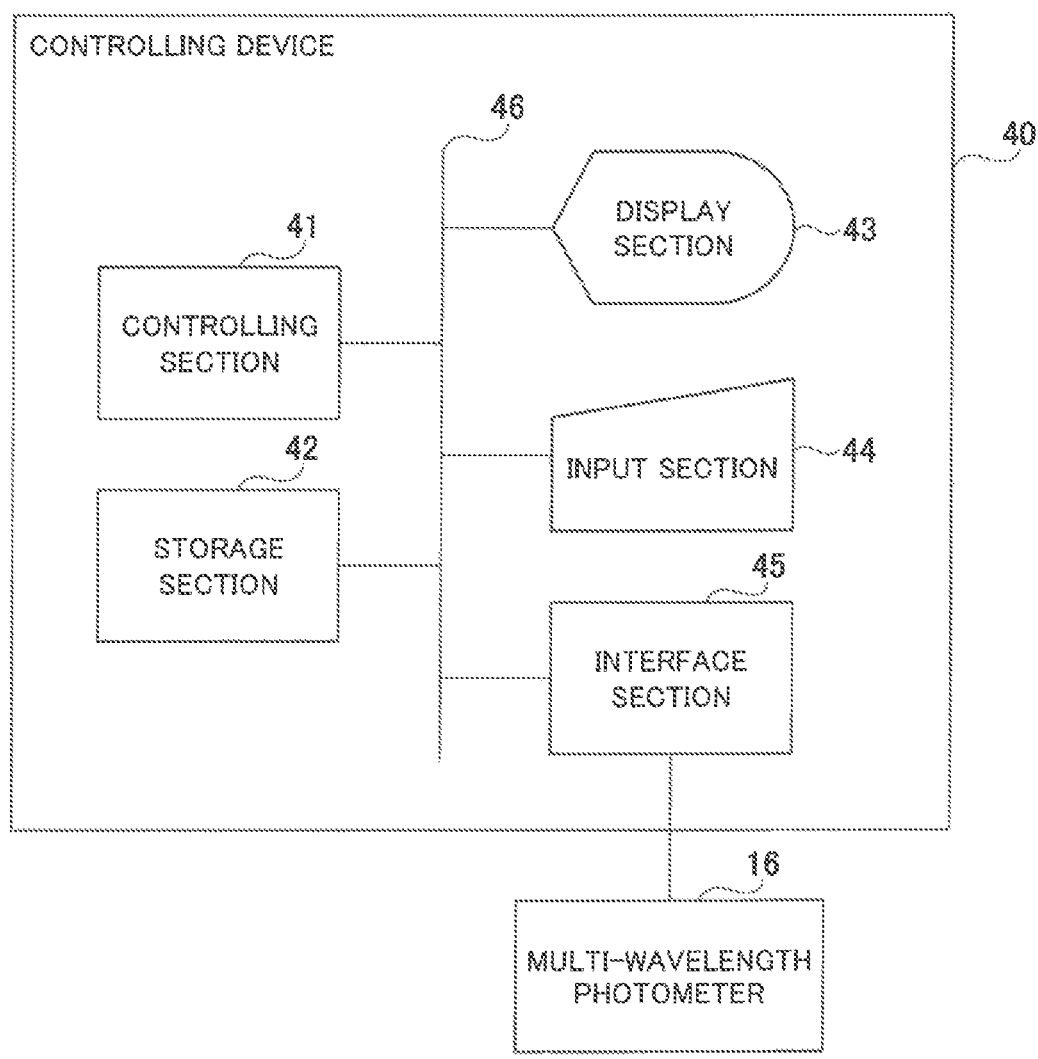
FIG. 3 is a block diagram of an example of an internal structure of a controlling device according to the first embodiment of the present invention.

FIG. 3 is a block diagram of an example of an internal structure of the controlling device 40.

The controlling device 40 includes the controlling section 41, a storage section 42, a display section 43, an input section 44, and an interface section 45, which are connected to a bus 46.

The controlling section 41 is formed from a CPU (Central Processing Unit), and controls the operation of each portion in the biochemical analyzer 1 on the basis of a program read out from the storage section 42. The controlling section 41 displays that an original specimen contamination prevention operation is being performed on the display section 43. The details of various processing operations that are executed by the controlling section 41 are described later.

The storage section 42 is formed from a large-capacity recording device, such as an HDD (Hard disk drive), and records, for example, a program of the controlling section 41, calibration curves, parameters, and input operations performed by using the input section 44. The storage section 42 is used as an example of a non-transitory computer-readable recording medium that stores a program that is executed by the CPU.

The display section 43 displays, for example, the results of measurement of a liquid mixture of a specimen, a first reagent, and a second reagent. For example, a liquid crystal display device is used for the display section 43.

The input section 44 accepts an operation input that is performed by a user with respect to the biochemical analyzer 1, and outputs an input signal to the controlling section 41. For example, a mouse, a keyboard, or a touch panel is used for the input section 44.

When a measurement value of a liquid mixture measured by the multi-wavelength photometer 16 is input to the interface section 45, the interface section 45 transfers the measurement value to the controlling section 41. In FIG. 3, an example in which only the multi-wavelength photometer 16 is connected to the interface section 45 is shown. However, each portion in the biochemical analyzer 1 is also similarly connected to the interface section 45, and is controlled by the controlling device 40.

1-4. Example of Setting Screen

Next, an example of a structure of a setting screen of the display section 43 is described with reference to FIG. 4.

FIG. 4 is a structural view of a specimen contamination prevention setting screen P1.

The specimen contamination prevention setting screen P1 is a screen for setting, for example, an operation for preventing contamination of an original specimen and the number of cleaning operations. An inter-specimen carry-over prevention operation that is set on the setting screen P1 is an operation for preventing contamination of an original specimen caused by the original specimen sampling probe 7.

When a specimen having a high viscosity or a specimen having a high value (a specimen to which an extremely high value is given) is used, by performing an operation of cleaning the original specimen sampling probe 7 with a cleaning agent a plurality of times, it is possible to prevent contamination caused by an original specimen adhered to the original specimen sampling probe 7. The controlling section 41 controls the cleaning operation of the original specimen sampling probe 7 in accordance with the type of cleaning agent and the number of cleaning operations, which are set via the setting screen P1.

The setting screen P1 includes a probe cleaning check field, a cleaning agent number field, and the number-of-cleaning-operations field.

In the probe cleaning check field, ON or OFF is set with regard to the setting of cleaning of the original specimen sampling probe 7.

In the cleaning agent number field, the cleaning operation of the original specimen sampling probe 7 is set (the cleaning agent to be used or a cleaning operation using the internal water W1 of the original specimen sampling probe 7 is set).

In the number-of-cleaning-operations field, the number of cleaning operations is set.

Then, after the original specimen sampling probe 7 has dispensed a specimen into a dilution container 23, in accordance with an inter-specimen carry-over prevention operation that is set via the setting screen P1, the controlling section 41 performs control to clean the original specimen sampling probe 7 with a cleaning agent sucked in from a sample container 21 or the cleaning agent coming-out port 31a.

1-5. Example of Processing for Performing Original Specimen Contamination Prevention Operation Next, a case in which after the original specimen sampling probe 7 has dispensed a specimen A into a dilution container 23 from a sample container 21 that contains the specimen A, a specimen B is dispensed into a dilution container 23 from a sample container 21 that contains the specimen B is considered. The specimens A and B and specimens C and D are examples of original specimens.

When, with the specimen A adhered to the original specimen sampling probe 7, the original specimen sampling probe 7 is inserted into the sample container 21 that contains the specimen B, an original specimen contamination where the specimen B is contaminated by the specimen A occurs. When the original specimen contamination occurs, the results of measurement of the specimen B is affected by the specimen A, as a result of which the correct measurement results can no longer be obtained.

In order to prevent such original specimen contamination, the original specimen sampling probe 7 that has dispensed the specimen A needs to be cleaned before dispensing the specimen B. As described above, the cleaning agent used in cleaning the original specimen sampling probe 7 is discarded by being discharged to a dilution container 23 or to the original specimen sampling probe cleaning mechanism 31. However, in order to prevent the processing capability of the biochemical analyzer 1 from being reduced, it is desirable that the cleaning agent used in cleaning the original specimen sampling probe 7 be discharged to the original specimen sampling probe cleaning mechanism 31. In the description below, an operation of discharging the cleaning agent to the original specimen sampling probe cleaning mechanism 31 by the original specimen sampling probe 7 is described.

Here, processing for the original specimen contamination prevention operation is described.

FIG. 5 is an explanatory view showing that, after the biochemical analyzer 1 has measured the specimen A, the original specimen contamination prevention operation is required when measuring the specimen B. FIG. 5 shows a device operation cycle, a dilution container original specimen dispensing operation, an operation of the original specimen sampling probe 7, a stirring operation, a dilution container diluted specimen dispensing operation, and an operation of the diluted specimen sampling probe 8.

The device operation cycle column shows the operation cycles of the biochemical analyzer 1 by down arrows. The cycle numbers (1) to (7) are added next to the corresponding down arrows.

The dilution container original specimen dispensing operation column shows the number of dispensing operation steps in one cycle when the original specimen sampling probe 7 dispenses an original specimen into a dilution container 23; and the dilution container original specimen dispensing operation is performed in conformity with a sucking operation at the original specimen sampling probe 7.

The original specimen sampling probe column shows the types of specimen that are dispensed into a dilution container 23 where the original specimen sampling probe 7 has reached a specimen discharge position and cleaning operations of the original specimen sampling probe 7. In cycle (1), the original specimen sampling probe 7 dispenses the specimen A into a dilution container 23. In cycle (2), after the original specimen sampling probe 7 has sucked in a cleaning agent from a sample container 21 or the cleaning agent coming-out port 31a and has been cleaned, the cleaning agent is discharged to the original specimen sampling probe cleaning mechanism 31 (such an operation is called a "cleaning operation of the original specimen sampling probe 7"). Next, in cycle (3), the specimen B is dispensed into a different dilution container 23, and, in cycle (4), the cleaning operation of the original specimen sampling probe 7 is performed again. In this way, the original specimen sampling probe 7 repeats the operation of dispensing a specimen into a dilution container 23 in a certain cycle and the operation of cleaning the original specimen sample probe 7 in a next cycle.

The stirring operation column shows the operation of stirring a cleaning agent or a specimen dispensed into a dilution container 23 by the dilution stirring mechanism 9. In cycle (1), a specimen Z dispensed into a dilution container 23 is stirred. In cycle (2), the specimen A is stirred. In cycle (3), a standby operation is performed. Next, in cycle (4), the specimen B is stirred. In cycle (5), a standby operation is performed. In this way, the operation of stirring a specimen dispensed into a dilution container 23 in a certain cycle and the standby operation in the next cycle are repeated.

The dilution container diluted specimen dispensing operation column shows the number of steps of dispensing operations in one cycle when the diluted specimen sampling probe 8 dispenses a diluted specimen that is contained in a dilution container 23 into a reaction container 26; and the dilution container diluted specimen dispensing operation is performed in conformity with a sucking operation of the diluted specimen sampling probe 8.

The diluted specimen sampling probe column shows a dispensing operation of sucking in a diluted specimen in a dilution container 23 by the diluted specimen sampling probe 8. In order to perform a measurement item (1) in cycle (3), the diluted specimen sampling probe 8 dispenses a diluted specimen of the specimen A that is contained in a dilution container 23 into a reaction container 26. In order to perform a measurement item (2) in cycle (4), the diluted specimen sampling probe 8 dispenses the diluted specimen of the specimen A into a different reaction container 26. In order to perform a measurement item (3) in cycle (5), the diluted specimen sampling probe 8 dispenses the diluted specimen of the specimen A into a different reaction container 26.

Similarly, in order to perform a measurement item (1) in cycle (6), the diluted specimen sampling probe 8 dispenses a diluted specimen of the specimen B that is contained in a dilution container 23 into a reaction container 26. In order to perform a measurement item (2) in cycle (7), the diluted specimen sampling probe 8 dispenses the diluted specimen of the specimen B into a different reaction container 26.

Here, the cleaning operation of the original specimen sampling probe 7 that is performed in each of cycles (2), (4), and (6) is an operation that interrupts the usual measurement operations. Therefore, the operation of dispensing a specimen is delayed by one cycle for every one cleaning operation. Further, the time required for the inter-specimen carry-over prevention operation is not necessarily a fixed time.

However, specimens to be measured by the biochemical analyzer 1 are generally such that a plurality of measurement items are measured per specimen. In addition, the biochemical analyzer 1 includes a diluting mechanism for diluting a specimen (the dilution turntable 3, the diluted specimen sampling probe 8, the dilution stirring mechanism 9, the dilution container cleaning mechanism 11, and the dilution containers 23). Therefore, as long as it is during the time in which the diluted specimen sampling probe 8 is performing the operation of dispensing a specimen over a plurality of cycles, even if the cleaning operation of the original specimen sampling probe 7 is being performed, the processing operations of the measurement items are not affected. As a result, it is possible to clean the original specimen sampling probe 7 and prevent contamination of an original specimen without reducing the processing capability of the biochemical analyzer 1.

In the biochemical analyzer 1 according to the first embodiment described above, in order to prevent contamination of an original specimen, it is possible to clean the original specimen sampling probe 7 by using a cleaning agent sucked in from a sample container 21 or the cleaning agent coming-out port 31a. Therefore, it is possible to prevent contamination of an original specimen that is to be measured at a facility that uses the biochemical analyzer 1 and to execute high-level biochemical analyses.

As shown in FIG. 5, even if the original specimen sampling probe 7 causes interruption by its cleaning operation, the operation of dispensing a diluted specimen into a reaction container 26 from a dilution container 23 by the diluted specimen sampling probe 8 is not hindered. In addition, the processing capability of the biochemical analyzer 1 is directly affected by the operation of dispensing a diluted specimen into a reaction container 26 from a dilution container 23 by the diluted specimen sampling probe 8. Therefore, as long as the operation of the diluted specimen sampling probe 8 is not hindered, the processing capability of the biochemical analyzer 1 is not reduced. Consequently, in the biochemical analyzer 1, it is possible to sufficiently clean the original specimen sampling probe 7 to an extent that contamination of an original specimen caused by the effect of an inter-specimen carry-over does not occur, and to prevent the original specimen from becoming contaminated.

After the cleaning operation of the original specimen sampling probe 7 has been performed, the cleaning agent that has been used in the cleaning is discharged to the original specimen sampling probe cleaning mechanism 31 to discard it. Therefore, only the specimen is dispensed into a dilution container 23 without the cleaning agent being discharged to the dilution container 23 after cleaning the original specimen sampling probe 7. Since the cleaning agent is not discharged to the dilution container 23, the operation of cleaning the diluted specimen sampling probe 8 and the operation of cleaning the stirring rods of the dilution stirring mechanism 9, which are performed by using a cleaning agent contained in a dilution container 23, no longer need to be performed as they were hitherto performed. However, since the dilution container 23 only contains a diluted specimen, and is used in the measurement, the efficiency with which the dilution containers 23 are used (the number of dilution containers 23 containing a specimen/the total number of dilution containers 23) is not reduced.

However, the original specimen sampling probe 7 may discharge a cleaning agent sucked in from a sample container 21 or the cleaning agent coming-out port 31a to a dilution container 23 without discharging the cleaning agent to the original specimen sampling probe cleaning mechanism 31. By control of the controlling section 41, the operation of discarding a cleaning agent to a dilution container 23 by the original specimen sampling probe 7 may be performed in the same cycle as the cleaning operation of the original specimen sampling probe 7 shown in the original specimen sampling probe column in FIG. 5.

Second Embodiment

In the original specimen contamination prevention operation according to the above-described first embodiment, since the number of cleaning operations of the original specimen sampling probe 7 is less than the number of measurement items for each specimen, the processing capability of the automatic analyzer is not affected. However, the number of cleaning operations of the original specimen sampling probe 7 and the number of cleaning operations of the original specimen sampling probe 7 in accordance with the number of measurement items may be increased or decreased.

2-1. Example of Dilution Container Cleaning Operation

FIGS. 6A and 6B are each an explanatory view showing that, after a biochemical analyzer 1 has measured a specimen A, an original specimen sampling probe 7 is cleaned a plurality of times before dispensing a specimen B.

The device operation cycle column in FIG. 6A shows cycles (1) to (8).

In the original specimen sampling probe 7 column, in cycle (1), an operation of dispensing the specimen A is performed; and, in cycle (2), a first cleaning operation of the original specimen sampling probe 7 (an operation in which, after the original specimen sampling probe 7 has sucked in a cleaning agent from a sample container 21 or a cleaning agent coming-out port 31a, and the original specimen sampling probe 7 has been cleaned, the cleaning agent is discharged to an original specimen sampling probe cleaning mechanism 31) is performed. Similarly, in cycle (3), a second cleaning operation is performed; in cycle (4), a third cleaning operation is performed; and in cycle (5), a fourth cleaning operation is performed. Thereafter, in cycle (6), an operation of dispensing the specimen B into a different dilution container 23 is performed. Then, in cycle (7), the first cleaning operation is performed again; and, in cycle (8), an operation of dispensing a specimen C into a different dilution container 23 is performed.

The stirring operation column shows that, in cycle (2), an operation of stirring the specimen A dispensed into a dilution container 23 is performed; in cycles (3) to (6), nothing is performed; and, in cycle (7), an operation of stirring the specimen B dispensed into a dilution container 23 is performed.

The diluted specimen sampling probe column shows that, in cycle (3), a dispensing operation (measurement item 1) is performed; in cycle (4), a dispensing operation (measurement item 2) is performed; and, in cycle (5), a dispensing operation (measurement item 3) is performed. Until the specimen B is dispensed and stirred, a diluted specimen sampling probe 8 cannot dispense a diluted specimen into a reaction container 26 from a dilution container 23. Therefore, in cycles (6) and (7), the operation of the diluted specimen sampling probe 8 is stopped. In this way, when the cleaning operation of the original specimen sampling probe 7 is performed a plurality of times, since the diluted specimen sampling probe 8 cannot dispense a diluted specimen from a dilution container 23 to a reaction container 26, the processing capability of the biochemical analyzer 1 may be reduced. Therefore, the controlling section 41 performs control to reduce the number of cleaning operations of the original specimen sampling probe so as to be within a time in which the diluted specimen sampling probe 8 dispenses a diluted specimen into a reaction container 26 in accordance with a measurement item.

FIG. 6B shows an operation when the number of cleaning operations of the original specimen sampling probe 7 is reduced. Here, the controlling section 41 is capable of increasing or decreasing the number of cleaning operations of the original specimen sampling probe 7 so as not to reduce the processing capability of the biochemical analyzer 1. As described above, the processing capability of the biochemical analyzer 1 depends upon the operation of dispensing a diluted specimen into a reaction container 26 from a dilution container 23 by the diluted specimen sampling probe 8. Therefore, the controlling section 41 controls the number of cleaning operations of the original specimen sampling probe 7 such that there is no gap between the operations of dispensing a diluted specimen by the diluted specimen sampling probe 8. For example, the controlling section 41 reduces the number of cleaning operations of four in cycles (2) to (5) shown in FIG. 6A to the number of cleaning operations of two in cycles (2) and (3) shown in FIG. 6B. This makes it possible to suppress a reduction in the processing capability of the biochemical analyzer 1 while ensuring the number of cleaning operations of the original specimen sampling probe 7 to the extent possible.

In the biochemical analyzer 1 according to the second embodiment described above, the controlling section 41 sets the number of cleaning operations to that allowing the suppression of a reduction in the processing capability of the biochemical analyzer 1 to clean the original specimen sampling probe 7. This makes it possible to clean the original specimen sampling probe 7 to an extent that does not interfere with the preventing of contamination of an original specimen and that does not reduce the processing capability of the biochemical analyzer 1, so that it is possible to prevent contamination of the original specimen.

For example, a warning or information that notifies to a user operating the biochemical analyzer 1 that the number of cleaning operations of the original specimen sampling probe 7 has been reduced may be displayed on the display section 43. This allows the user to consider that the number of cleaning operations of the original specimen sampling probe 7 has been reduced and the possibility of the occurrence of contamination of an original specimen.

Third Embodiment

Figure 7:
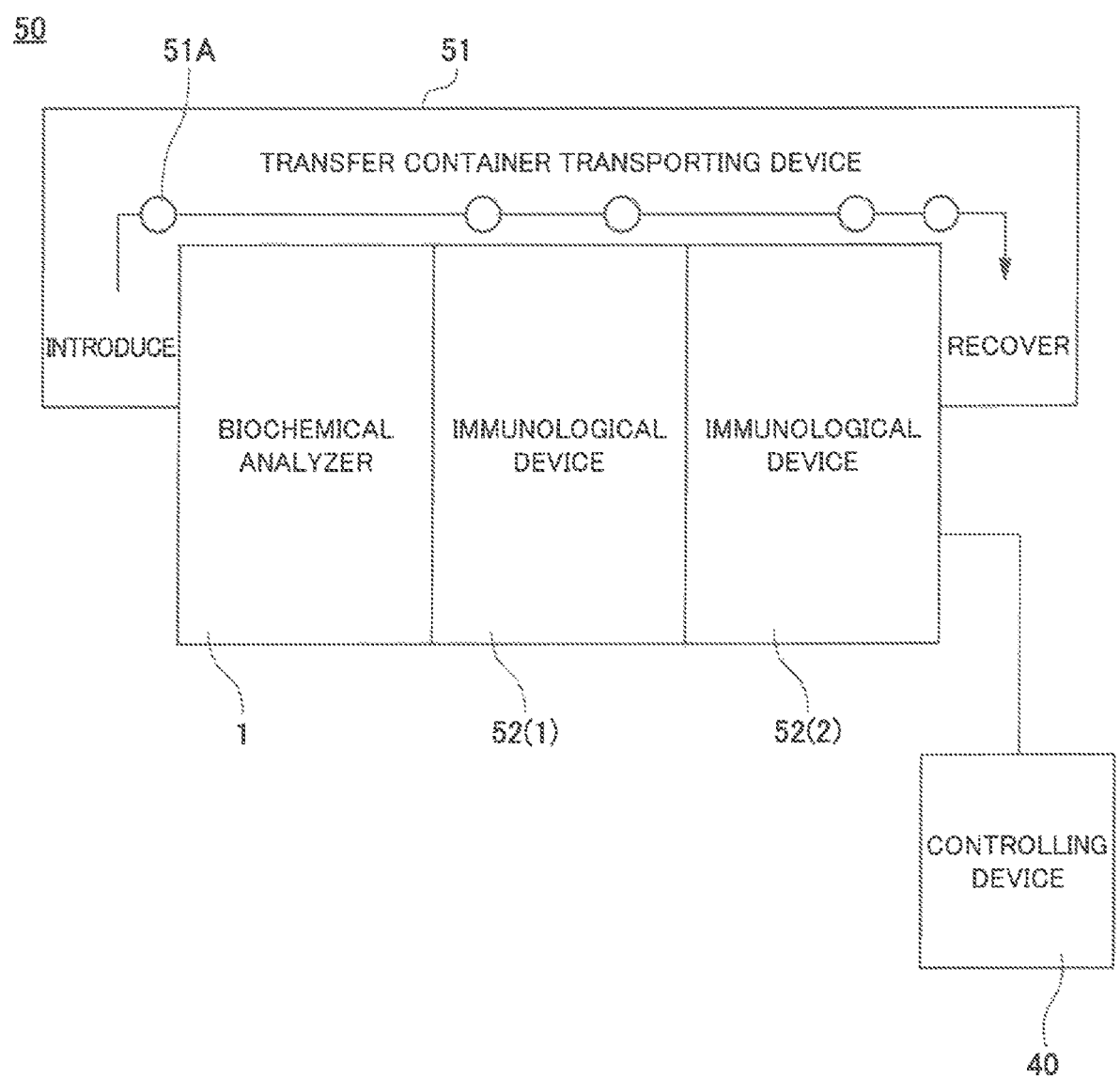
FIG. 7 is an explanatory view of an example of a structure of an automatic analyzing system according to a third embodiment of the present invention.

FIG. 7 is an explanatory view of an example of a structure of an automatic analyzing system 50.

In each of the above-described embodiments, original specimens are only contained in sample containers 21 of the biochemical analyzer 1. However, devices other than the biochemical device 1 (such as immunological devices) sometimes need to measure the same specimen analyzed by the biochemical analyzer 1. In this case, the biochemical analyzer 1 and the devices other than the biochemical device 1 are connected to each other to continuously analyze the specimen.

The automatic analyzing system 50 shown in FIG. 7 includes, in addition to the above-described biochemical analyzer 1, a transfer container transporting device 51, immunological devices 52(1) and 52(2), and a controlling device 40.

The transfer container transporting device 51 has a function of, when a transfer container 51A that contains an original specimen is introduced, recovering the transfer container 51A after the transfer container 51A that has been introduced to the biochemical analyzer 1, the immunological device 52(1), and the immunological device 52(2) in that order has been transported between the devices. Then, the operation of each device of the automatic analyzing system 50 and the operation of the transfer container transporting device 51 are controlled by a controlling section 41 of the controlling device 40. Therefore, the controlling section 41 performs control to dispense into a dilution container 23 the specimen contained in the transfer container 51A that is transported to the biochemical analyzer 1 and other automatic analyzers by the transfer container transporting device 51.

The biochemical analyzer 1 is capable of performing a biochemical analysis by dispensing an original specimen from the transfer container 51A that is transported by the transfer container transporting device 51. Since the original specimen is contained in the transfer container 51A, the biochemical analyzer 1 need not include the above-described sample turntable 2 and sample containers 21. Since the original specimen sampling probe 7 that has been cleaned by the cleaning operation in the first embodiment and the second embodiment does not contaminate the original specimen that is contained in the transfer container 51A, the analyses at the immunological devices 52(1) and 52(2) that follow are not affected thereby.

The immunological devices 52(1) and 52(2) are provided together with the biochemical analyzer 1, and are used as examples of automatic analyzers. An original specimen is dispensed into each of the immunological devices 52(1) and 52(2) from the transfer container 51A that is transported by the transfer container transporting device 51 to perform the necessary analyses thereat. Similarly to the original specimen sampling probe 7 of the biochemical analyzer 1, it is desirable that each of the immunological devices 52(1) and 52(2) include a probe that is capable of preventing contamination of the original specimen. In addition, since contamination of the original specimen that is contained in the transfer container 51A is prevented, similarly to the biochemical analyzer 1, it is possible to perform high-level analyses of the original specimen even at the immunological devices 52(1) and 52(2).

In the third embodiment described above, the original specimen contained in the transfer container 51A that is transported between the devices by the transfer container transporting device 51 is not contaminated by the original specimen sampling probe 7 of the biochemical analyzer 1. Therefore, high-level measurement results can be acquired by analyses using an uncontaminated original specimen not only at the biological analyzer 1 but also at the immunological devices 52(1) and 52(2), which are devices other than the biochemical analyzer 1.

The present invention is not limited to the above-described embodiments, and various application examples and modifications are obviously possible without departing from the gist of the present invention that is described in the scope of the claims.

For example, the above-described embodiments are detailed and specific descriptions of the structures of the device and the system for making it easier to understand the present invention, and do not limit the present invention to that including all of the structures that have been described. In addition, part of the structure of an embodiment described here may be replaced by the structure of another embodiment. Further, the structure of a certain embodiment may have the structure of another embodiment added thereto. Further, part of the structure of each embodiment may have another structure added thereto, may be deleted, or may be replaced.

Control lines and information lines that are considered necessary for the description are indicated, and are not necessarily all of the control lines and information lines in terms of products. Actually, it may be considered that almost all of the structures are connected to each other.

What is claimed is:

1. An automatic analyzer comprising:
a specimen holding section that holds at least one specimen container for containing a specimen and at least one other specimen container;
a specimen dispensing section that dispenses the specimen from the specimen container into a dilution container;
a dilution container holding section that holds the dilution container for containing a diluted specimen, which is the specimen that has been diluted;
a diluted specimen dispensing section that dispenses the diluted specimen from the dilution container into a reaction container;
a first cleaning section positioned between the specimen holding section and the dilution container holding section for cleaning the specimen dispensing section;
a cleaning liquid supplying section that is arranged to supply a cleaning liquid to the specimen dispensing section and is disposed on a movement route of the specimen dispensing section at a position where the specimen dispensing section can suck the cleaning liquid that the cleaning liquid supplying section supplies;
an input section configured to accept a selection that is performed by a user to one of: a) discharge the cleaning liquid the specimen dispensing section has sucked in from the cleaning liquid supplying section to the first cleaning section; or b) discharge the cleaning liquid the specimen dispensing section has sucked in from the cleaning liquid supplying section to the dilution container; and
a controlling section configured to:
while the diluted specimen dispensing section dispenses the diluted specimen into the reaction container in accordance with a measurement item, cause the specimen dispensing section to perform a cleaning operation of the specimen dispensing section a number of times by using the cleaning liquid the specimen dispensing section has sucked in from the cleaning liquid supplying section, and to discharge the cleaning liquid the specimen dispensing section has sucked in from the cleaning liquid supplying section to the first cleaning section or to the dilution container, in accordance with the selection accepted in the input section, upon the input section accepting a selection to discharge the cleaning liquid the specimen dispensing section has sucked in from the cleaning liquid supplying section to the first cleaning section, cause the specimen dispensing section to discharge the cleaning liquid the specimen dispensing section has sucked in from the cleaning liquid supplying section to the first cleaning section so as to be discarded, and upon the input section accepting a selection to discharge the cleaning liquid the specimen dispensing section has sucked in from the cleaning liquid supplying section to the dilution container, cause the specimen dispensing section to discharge the cleaning liquid the specimen dispensing section has sucked in from the cleaning liquid supplying section to the dilution container.

2. The automatic analyzer according to dam 1, wherein the controlling section is further configured to cause the cleaning operation of the specimen dispensing section to be performed in accordance with the number of cleaning operations, which are set via a setting screen.

3. The automatic analyzer according to claim 1, wherein the controlling section is configured to perform control to reduce the number of cleaning operations of the specimen dispensing section so as to be within a time in which the diluted specimen dispensing section dispenses the diluted specimen into the reaction container in accordance with the measurement item.

4. The automatic analyzer according to claim 1, wherein the cleaning liquid supplying section is at least any one of the at least one other specimen container having the cleaning liquid contained therein, a coming-out port that is provided near the first cleaning section for dispensing the cleaning liquid, and a cleaning liquid container that is provided near the first cleaning section and that is for containing the cleaning liquid.

5. The automatic analyzer according to claim 1, wherein the controlling section is further configured to:

upon the input section accepting the selection to discharge the cleaning liquid the specimen dispensing section has sucked in from the cleaning liquid supplying section to the dilution container, cause the specimen dispensing section to discharge the cleaning liquid the specimen dispensing section has sucked in from the cleaning liquid supplying section to the dilution container, and the diluted specimen dispensing section to suck in the cleaning liquid from the dilution container containing the cleaning liquid discharged from the specimen dispensing section.

6. A computer-readable recording medium that stores a program configured to cause a computer to perform control of an automatic analyzer comprising:

a specimen holding section that holds a specimen container for containing a specimen;

a specimen dispensing section that dispenses the specimen from the specimen container into a dilution container;

a dilution container holding section that holds the dilution container for containing a diluted specimen, which is the specimen that has been diluted;

a diluted specimen dispensing section that dispenses the diluted specimen from the dilution container into a reaction container;

a first cleaning section positioned between the specimen holding section and the dilution container holding section for cleaning the specimen dispensing section;

a cleaning liquid supplying section that is arranged to supply a cleaning liquid to the specimen dispensing section and is disposed on a movement route of the specimen dispensing section at a position where the specimen dispensing section can suck the cleaning liquid that the cleaning liquid supplying section supplies; and an input section configured to accept a selection that is performed by a user to one of: a) discharge the cleaning liquid the specimen dispensing section has sucked in from the cleaning liquid supplying section to the first cleaning section; or b) discharge the cleaning liquid the specimen dispensing section has sucked in from the cleaning liquid supplying section to the dilution container, the program configured to cause the computer to:

while the diluted specimen dispensing section dispenses the diluted specimen into the reaction container in accordance with a measurement item, cause the specimen dispensing section to perform a cleaning operation of the specimen dispensing section a number of times by using the cleaning liquid the specimen dispensing section has sucked in from the cleaning liquid supplying section, and to discharge the cleaning liquid the specimen dispensing section has sucked in from the cleaning liquid supplying section to the first cleaning section or to the dilution container, in accordance with the selection accepted in the input section, upon the input section accepting a selection to discharge the cleaning liquid the specimen dispensing section has sucked in from the cleaning liquid supplying section to the first cleaning section, cause the specimen dispensing section to discharge the cleaning liquid the specimen section so as to be discarded, and upon the input section accepting a selection to discharge the cleaning liquid the specimen dispensing section has sucked in from the cleaning liquid supplying section to the dilution container.

* * * * *